United States Patent
Thomson et al.

(10) Patent No.: US 6,728,335 B1
(45) Date of Patent: Apr. 27, 2004

(54) CONTROLLER FOR ARRAY OF MINIATURE RADIATION SOURCES

(75) Inventors: Euan Thomson, Harvard, MA (US); Mark Dinsmore, Sudbury, MA (US)

(73) Assignee: Carl-Zeiss-Stiftung, Oberkochen (DE)

( * ) Notice: Subject to any disclaimer, the term of this patent is extended or adjusted under 35 U.S.C. 154(b) by 0 days.

(21) Appl. No.: 10/133,048

(22) Filed: Apr. 26, 2002

Related U.S. Application Data
(60) Provisional application No. 60/351,809, filed on Jan. 25, 2002.

(51) Int. Cl.[7] .................................................. A61N 5/10
(52) U.S. Cl. ........................... 378/65; 378/64; 378/92; 378/124; 378/134; 600/2; 600/3
(58) Field of Search ................................ 378/64, 65, 92, 378/101, 109, 110, 111, 112, 124, 134, 136; 600/2, 3; 607/100, 113

(56) References Cited

U.S. PATENT DOCUMENTS

| | | | | |
|---|---|---|---|---|
| 4,584,991 A | * | 4/1986 | Tokita et al. .................. | 600/3 |
| 4,815,449 A | * | 3/1989 | Horowitz ....................... | 600/7 |
| 5,729,583 A | | 3/1998 | Tang et al. ................... | 378/122 |
| 5,817,021 A | | 10/1998 | Reichenberger ............. | 600/439 |
| 6,443,978 B1 | * | 9/2002 | Zharov ......................... | 607/91 |
| 6,449,336 B2 | * | 9/2002 | Kim et al. .................... | 378/65 |
| 6,556,651 B1 | * | 4/2003 | Thomson et al. ............. | 378/65 |
| 6,623,418 B2 | * | 9/2003 | Smith ............................ | 600/3 |
| 2002/0099428 A1 | * | 7/2002 | Kaufman ..................... | 607/101 |
| 2002/0110220 A1 | * | 8/2002 | Shen et al. .................. | 378/124 |
| 2003/0093130 A1 | * | 5/2003 | Stypulkowski ............... | 607/46 |

FOREIGN PATENT DOCUMENTS

WO    WO 02/41947 A2    5/2002

\* cited by examiner

Primary Examiner—Edward J. Glick
Assistant Examiner—Allen C Ho
(74) Attorney, Agent, or Firm—McDermott, Will & Emery

(57) ABSTRACT

A controller is provided for selectively and independently control each of a plurality of therapeutic radiation sources arranged along an array. The controller is operable to selectively generate therapeutic radiation at selected time intervals and at selected intensities. The controller includes intensity control circuitry for controlling the intensity of the therapeutic radiation generated by each therapeutic radiation source. The controller also includes duration control circuitry for controlling the duration of the therapeutic radiation generated by each therapeutic radiation source. The controller may also include a mechanical introducer for inserting the array into a treatment region, and for withdrawing the array from the treatment region.

32 Claims, 6 Drawing Sheets

CONTROLLER FOR ARRAY OF MINIATURE RADIATION SOURCES

CROSS-REFERENCE TO RELATED APPLICATIONS

This application claims benefit of U.S. Provisional Application Ser. No. 60/351,809, entitled "Array of Miniature Radiation Sources" and filed on Jan. 25, 2002.

STATEMENT REGARDING FEDERALLY SPONSORED RESEARCH

Not Applicable

REFERENCE TO MICROFICHE APPENDIX

Not Applicable

FIELD OF THE INVENTION

The present invention relates to a controller for an array of miniature therapeutic radiation sources.

BACKGROUND OF THE INVENTION

In the field of medicine, radiation may be used for diagnostic, therapeutic and palliative purposes. Therapeutic use of radiation such as x-rays and γ-rays typically involves using these rays to eradicate malignant cells. Conventional radiation treatment systems used for medical treatment, such as linear accelerators that produce high-energy x-rays, utilize a remote radiation source external to the targeted tissue. A beam of radiation is directed at the target area, for example a malignant tumor inside the body of a patient. The x-rays penetrate the patient's body tissue and deliver radiation to the cancer cells, usually seated deep inside the body. This type of treatment is referred to as teletherapy because the radiation source is located at some distance from the target. This treatment suffers from the disadvantage that tissue disposed between the radiation source and the target is exposed to radiation. To reach the cancer cells, the x-rays from an external radiation source must usually penetrate through normal surrounding tissues. Non-cancerous tissues and organs are thus also damaged by the penetrating x-ray radiation.

Brachytherapy, on the other hand, is a form of treatment in which the source of radiation is located close to, or in some cases within, the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of "seeds," i.e. encapsulated radioactive isotopes, which can be placed directly within or adjacent to the target tissue that is being treated. Handling and disposal of such radioisotopes, however, may impose considerable hazards to both the handling personnel and the environment. Also, introduction of the radioisotopes requires invasive procedures which have potential side-effects, such as the possibility of infection. Moreover, there is no ability to provide selective control of time dosage or radiation intensity.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body, is disclosed in U.S. Pat. No. 5,153,900 issued to Nomikos et al., U.S. Pat. No. 5,369,679 to Sliski et al., U.S. Pat. No. 5,422,926 to Smith et al., and U.S. Pat. No. 5,428,658 to Oettinger et al., all owned by the assignee of the present application, all of which are hereby incorporated by reference.

The x-ray brachytherapy system disclosed in the above-referenced patents includes a miniaturized, insertable probe capable of producing low power x-ray radiation while positioned within or in proximity to a predetermined region to be irradiated. In this way, x-ray radiation need not pass through the patient's skin, bone, or other tissue prior to reaching the target tissue. The probe may be fully or partially implanted into, or surface-mounted onto a desired area within a treatment region of a patient. X-rays are emitted from a nominal, or effective "point" source located within or adjacent to the desired region to be irradiated, so that substantially only the desired region is irradiated, while irradiation of other regions are minimized. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy treatment generally involves positioning the insertable probe into or adjacent to the tumor or the site where the tumor or a portion of the tumor was removed to treat the tissue adjacent the site with a local boost of radiation. X-ray probes of the type generally disclosed in U.S. Pat. No. 5,153,900 include a capsule, and a hollow, tubular probe or catheter extending from the capsule along an axis, and having an x-ray emitting target element at its distal end. The probe may enclose an electron source, such as a thermionic cathode. In one form of a thermionic cathode, a filament is resistively heated with a current. This in turn heats the cathode so that electrons are generated by thermionic emission.

In another form of an x-ray brachytherapy device, as disclosed in U.S. Pat. No. 5,428,658, an x-ray probe may include a flexible probe, such as a flexible fiber optic cable enclosed within a metallic sheath. The x-ray probe may also include a substantially rigid, evacuated capsule that is coupled to a distal end of the flexible probe. The capsule encloses an optically activated electron source, such as a photocathode, and an x-ray emissive target element. In a photocathode configuration, a photoemissive substance is irradiated by a LED or a laser source, causing the generation of free electrons. Typically, a flexible fiber optic cable couples light from a laser source or a LED to the photocathode.

U.S. Pat. No. 6,480,568 entitled "Optically Driven Therapeutic Radiation Source," issued on Nov. 12, 2002 to Mark Dinsmore, and hereby incorporated by reference in its entirety)(hereinafter the "'568 patent") discloses an optically driven (for example, laser driven) therapeutic radiation source using a reduced-power, increased efficiency electron source, which generates electrons with minimal heat loss. The '568 patent discloses the use of laser energy to heat an electron emissive surface of a thermionic emitter, instead of using an electric current to ohmically heat an electron emissive surface of a thermionic emitter. With the optically driven thermionic emitter, electrons can be produced in a quantity sufficient to produce the electron current necessary for generating therapeutic radiation at the target, while significantly reducing the requisite power requirements. U.S. patent application Ser. No. 10/005,290 and hereby incorporated by reference)(hereinafter the "290" application) discloses a therapeutic radiation source having an in situ radiation detector, which permits real-time monitoring of the therapeutic radiation that has been generated and delivered.

Even though the above-discussed miniature radiation sources can generate x-rays local to the target tissue, it is difficult to provide a uniform, or other desired, dose of radiation to an irregularly shaped target tissue, using these radiation sources. These miniature radiation sources generally act as point sources of therapeutic radiation. The intensity of the radiation from a point source decreases uniformly with approximately the square of the distance (R) from the source (i.e., $1/R^2$). Since body cavities, or the beds of resected tumors, are not generally spherically symmetrical, a point source within a body cavity or central to the resected tumor bed will not deliver a uniform dose of radiation to the tissue lining of the cavity or bed. Likewise, a point source at the center of a non-spherical tumor will not deliver radiation with an isodose contour matching the peripheral surface of the tumor.

The organs or body cavities being treated during radiation therapy usually have arbitrary and irregular shapes and geometries. The areas of a patient's body requiring treatment may be characterized by twists and bends. In some cases, the geometry of the target region may not be fixed, as in the bladder for example, which has a flexible inner wall without a well-defined shape. Also, some treatment procedures may require delivery of localized radiation to portions of the human body that are not easily accessible. Cancerous tumors are usually shaped irregularly, and are distributed randomly across a given anatomical region.

A single point source of therapeutic radiation, even when inserted into and activated within a patient's body, cannot deliver a uniform dose of radiation to a desired area within an irregularly shaped body cavity or organ, nor can it deliver more complex radiation dose patterns that may be desirable or required for some cases. Similarly, a single point source at the center of a non-spherical tumor will not deliver radiation with an isodose contour matching the peripheral surface of the tumor, as discussed earlier.

U.S. Pat. No. 6,556,651 (entitled "Array of Miniature Radiation Sources," issued on Apr. 29, 2003 to Euan Thomson and Mark Dinsmore, and hereby incorporated by reference in its entirety)(hereinafter the '651 patent), discloses a system for delivering therapeutic radiation that includes a plurality of point-like sources that are arranged over the desired treatment region as a one- or multi-dimensional array. A plurality of point radiation sources permits a more effective and versatile delivery of radiation over irregularly shaped treatment regions, as compared to a single point source of therapeutic radiation.

In order for a surgeon or other radiotherapy to use such an array of sources to build up complex, multi-dimensional dose patterns that he believes appropriate for the conditions of his patient, a controller is needed that can manipulate and selectively drive the array. There is a need for a controller that can control the intensity and duration of the therapeutic radiation emitted from each individual therapeutic radiation source in the array. The physician or other operator of the array of sources must be able to independently vary, for each therapeutic radiation source, parameters such as the turn-on time of the laser source, turn-on time of the high voltage source, the magnitude of the accelerating voltage provided to the electrons, and the magnitude of the electron beam current formed by the accelerated electrons.

SUMMARY OF THE INVENTION

The present invention is directed to a controller for an array of therapeutic radiation sources, for example x-ray sources. Each therapeutic radiation source includes an electron source and an associated target element. The controller allows each therapeutic radiation source to be selectively operated, so as to generate therapeutic radiation at selected time intervals and at selected intensities. The controller includes intensity control circuitry for independently controlling the intensity of the therapeutic radiation generated by each therapeutic radiation source. The controller also includes duration control circuitry for independently controlling the duration of the therapeutic radiation generated by each radiation source. The controller may also include means for controlling the position of each radiation source within the treatment region, for example a mechanical introducer for inserting the therapeutic radiation sources into a treatment region and withdrawing the radiation sources from the treatment region.

In one embodiment, each therapeutic radiation source is coupled to an associated fiber optical cable, so that the array of therapeutic radiation sources includes a plurality of fiber optical cables and a corresponding plurality of therapeutic radiation sources. Alternatively, a single fiber optical cable can be used, having one originating end and a plurality of terminating ends. Light is generated by an optical source and transmitted through a fiber optical cable, and impinges upon the electron source, causing emission of electrons. An accelerating voltage is provided between each electron source and each associated target element. The target element emits therapeutic radiation in response to incident accelerated electrons from the electron source. The generated electrons may form an electron beam along a beam path.

The intensity control circuitry may include programmable means for user-controlled adjustment of the amplitude of the accelerating voltage, or the magnitude of the current formed by the electron beam. The duration control circuitry may include means for selectively activating a high voltage power supply that provides the accelerating voltage between each electron source and its associated target element. The duration control circuitry may also include means for selectively activating the optical source.

The mechanical assembly may be an introducer for controllably effecting a reversible displacement of a linear or planar array of therapeutic radiation sources, into and out of a desired treatment region. Alternatively, the mechanical assembly may be an introducer that allows independent movement of each therapeutic radiation source with respect to each other.

The controller may regulate an in situ radiation detecting system that may be provided for monitoring in real time an amount of the therapeutic radiation emitted by each therapeutic radiation source. The controller may also regulate an image-guided surgery system that can generate in real time a visual image representing a cumulative dose of radiation delivered by each therapeutic radiation source to desired locations within the treatment region.

The present invention features a method for treating an anatomical region in a patient. The method includes positioning an array of x-ray sources near the anatomical region. For example, the array of x-ray sources may be inserted into a body passageway, such as a blood vessel, and the array may be guided through the body passageway so that each x-ray source is positioned at a desired location with respect to the anatomical region. The method includes selectively activating one or more of the x-ray sources in the array, so as to irradiate the anatomical region according to a desired and predetermined irradiation profile.

DETAILED DESCRIPTION

In overview, the present invention provides a controller for a therapeutic radiation system, formed of a plurality of miniaturized radiation sources that are strung together into an array. The controller enables the operator of the array to control the intensity of the therapeutic radiation to which a given area within the target tissue is exposed. The controller is also operable to control the length of time a given area within the target tissue is exposed to therapeutic radiation. The controller may also be operable to control the location of the radiation source within the target area that is receiving therapeutic radiation. For example, the controller may include one or more mechanical introducer assemblies for inserting the sources within, and withdrawing the sources from, the desired treatment region.

In a preferred embodiment of the invention, each therapeutic radiation source in the array is an electron-beam activated x-ray source which operates at relatively low voltages, i.e. approximately in the range of about 10 kV to about 90 kV, and relatively small electron beam currents, i.e. approximately in the range of about 1 nA to about 1 mA. At those operating voltages and currents, the x-ray output is relatively low, so that each therapeutic radiation source can be made small enough to be adapted for implantation in medical applications. In an embodiment in which the array of radiation sources is used for intravascular therapy, the x-ray source is preferably operated in the range of approximately 30 kV to about 40 kV.

In view of the low level x-ray output, adequate tissue penetration and cumulative dosage may be attained by locating the x-ray source adjacent to or within the region to be irradiated. Each miniature x-ray source may selectively apply a relatively low dose rate of x-rays to any part of a tumor, at any desired intensity level dictated by the clinical conditions of the region being treated. The x-rays may be applied for any desired time interval, either continually or periodically.

Figure 1A:
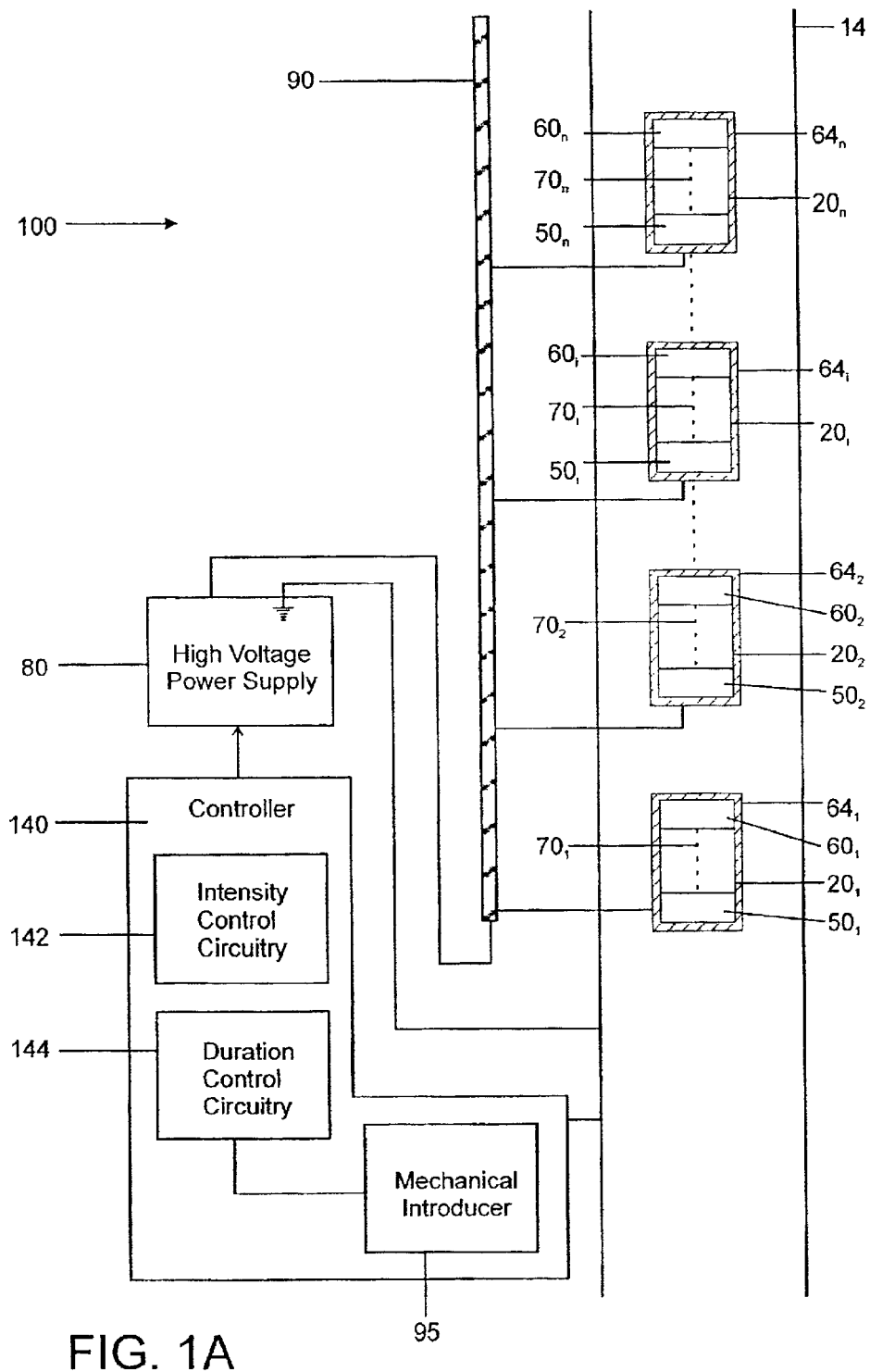
FIG. 1(a) is a schematic illustration of one embodiment of a controller for an array of therapeutic radiation sources, constructed according to the present invention.

FIG. 1(a) is a schematic illustration of one embodiment of a controller 140 for a system 100 for delivering therapeutic radiation, constructed according to the present invention. The system 100 includes a plurality of therapeutic radiation sources $20_1$, $20_2$, ..., $20_i$, ..., $20_n$. In the illustrated embodiment, the plurality of therapeutic radiation sources are shown as being arranged in a one-dimensional array, for simplicity. However, multi-dimensional arrays (i.e. planar, two-dimensional arrays, or higher-order arrays) are also within the scope of the present invention, as discussed in the '651 application. In the illustrated embodiment, the therapeutic radiation sources $20_n$ are x-ray sources, however, other types of therapeutic radiation sources are also within the scope of this invention.

In the illustrated embodiment, each x-ray source $20_i$ comprises an electron source $50_1$, and an associated target element $60_i$. Preferably, the electron source $50_i$ is a cathode. In particular, the cathode $50_i$ may be a resistively heated thermionic cathode, or a laser-heated thermionic cathode which emits electrons when heated to a sufficient temperature. Alternatively, the cathode $50_1$ may be a photocathode, which emits electrons by the photoelectric effect in response to an incident light beam. Alternatively, the cathode $50_i$ may be a cold cathode.

The system 100 includes means for providing an accelerating electric field which acts to accelerate electrons emitted from the electron source $50_i$ toward the target element $60_i$. The accelerating voltage may be provided by a high voltage power supply 80. In the illustrated embodiment, a single high voltage conductive cable 90 provides a connection to each electron source $50_i$ from the high voltage power supply 80. The single high voltage conductive cable 90 is tapped at different locations along the array, so as to connect the cathode $50_i$ in each x-ray source $20_i$ to the high voltage power supply 80. The outer flexible tube 14 couples a ground return from each target element $60_i$ to the high voltage power supply 80, thereby establishing a high voltage field between each cathode $50_i$ and each associated target element $60_i$. An insulator (not shown) provides insulation between the high voltage conductive cable 80 and the grounded flexible tube 14.

The controller 140 allows a surgeon or other radiation therapy professional to selectively operate each individual therapeutic radiation source $20_1$, so as to generate therapeutic radiation at selected time intervals and at selected intensities. The controller 140 includes intensity control circuitry 142 for independently controlling the intensity of the emitted x-rays from each individual therapeutic radiation source $20_i$, and duration control circuitry 144 for independently controlling the duration of the emission of the x-rays from each individual therapeutic radiation source $20_i$. In the illustrated embodiment, the controller 140 also includes a mechanical introducer 95 for appropriately positioning the array of radiation sources within a body passageway, and for guiding the array through the passageway.

Figure 1B:
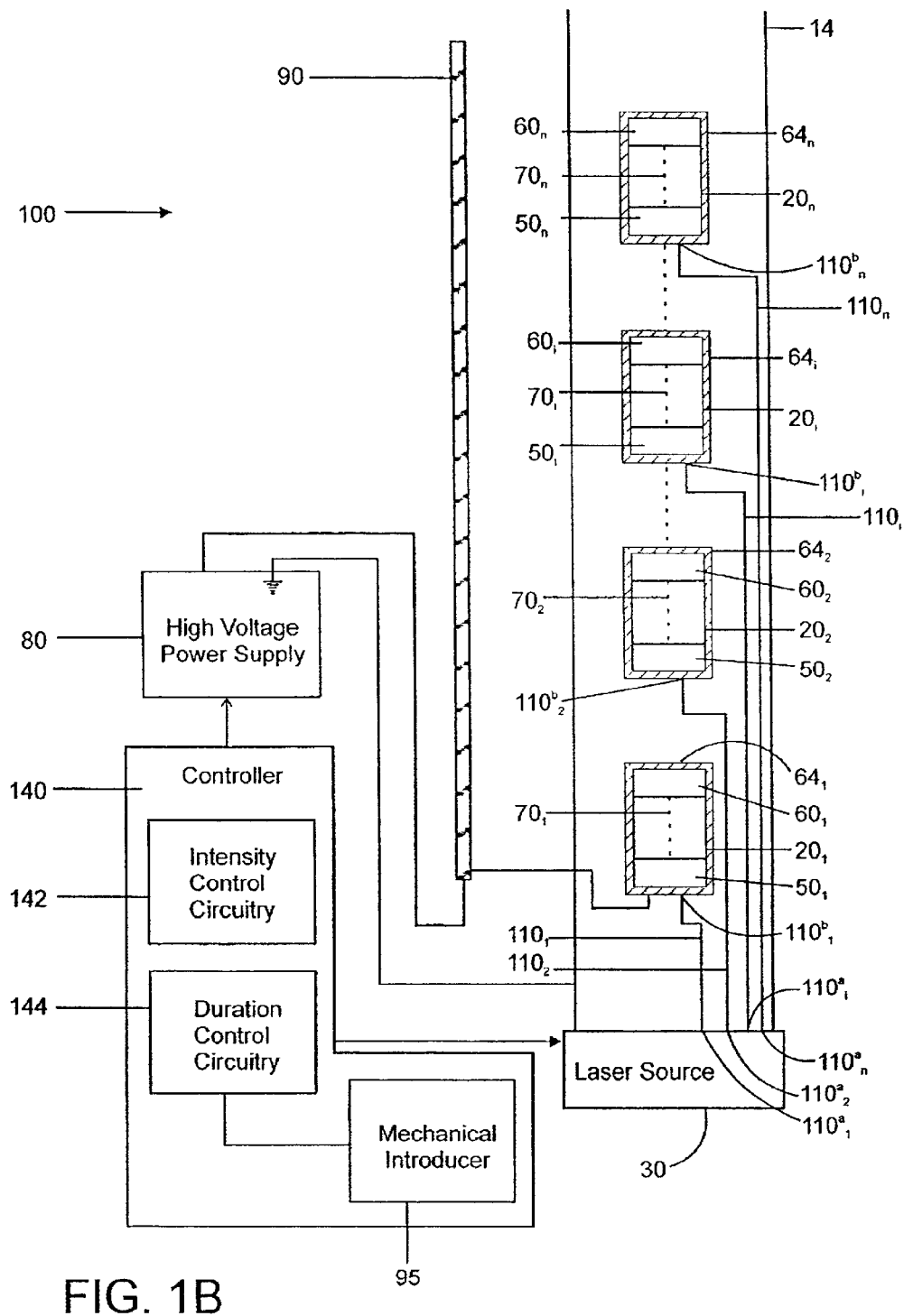
FIG. 1(b) is a schematic illustration of one embodiment of a controller for an array of therapeutic radiation sources, constructed according to the present invention, which includes a plurality of fiber optical cables and a corresponding plurality of therapeutic radiation sources.

FIG. 1(b) is a schematic illustration of another embodiment of the invention, in which the controller 140 is adapted for use with an array that includes a plurality of fiber optic cables $110_1$, ..., $110_i$, ..., $110_n$, and a corresponding plurality of therapeutic radiation sources $20_1$, ..., $20_i$, ..., $20_n$. Each fiber optical cable $110_i$ has an originating end $11_i{}^a$ and a terminating end $110_i{}^b$. Each x-ray source $20_i$ is coupled to the terminating end $110_i{}^b$ of an associated fiber optical cable $110_i$. A laser source 30 generates a laser beam directed to the originating end $110_i{}^a$ of each fiber optical cable $110_i$. Each fiber optical cable $110_i$ transmits optical radiation that is incident on the originating end $110_i{}^a$ of the fiber optical cable $110_i$ to the terminating end $110_i{}^b$ thereof. The electron source $50_i$ is responsive to incident laser light from the terminating end $110_i{}^b$ of the associated fiber optical cable $110_i$ to emit electrons.

In the embodiment illustrated in FIG. 1(b), the electron source $50_i$ may be a laser-heated thermionic cathode having an electron emissive surface. Electrons are emitted from the electron emissive surface of the thermionic cathode $50_i$ into the surrounding vacuum, when the surface is heated to a sufficient temperature. The thermionic cathode $50_i$ may be formed of a metallic material, including tungsten, thoriated tungsten, other tungsten alloys, and tantalum. The thermionic cathode $50_i$ may also be an oxide coated cathode.

In one form of the invention (not shown), a single optical fiber may be used to transmit light from the laser source 30 to the plurality of electron sources. Using fiber splicing techniques known in the art, an optical fiber having a single originating end and a plurality of terminating ends can be constructed to be used in the present invention.

Referring to the elements in FIGS. 1(*a*) and 1(*b*) in more detail, the target element $60_i$ includes an x-ray emissive element, for example a high atomic number element such as gold (Au) or tungsten (W), that emits x-rays in response to incident accelerated electrons from the electron beam. In the illustrated embodiment, the electrons emitted from the cathode $50_i$ generate an electron beam $70_i$ along a beam path. The associated target element $60_i$ is positioned in the electron beam path.

Each x-ray source $20_i$ may include a shell or capsule $64_i$ which encloses the cathode $50_i$ and the target element $60_i$. According to one embodiment, the capsule $64_i$ may be rigid in nature, and generally cylindrical in shape. In this embodiment, the cylindrical capsule $64_i$ enclosing the x-ray source $20_i$ can be considered to provide a substantially rigid housing for the cathode $50_i$ as well as for the target element $60_i$. The capsule $64_1$ defines a substantially evacuated interior region along a reference axis, between the cathode $50_1$ at an input end of the capsule $64_1$ and an x-ray transmissive window at an output end of the capsule. The material forming the capsule $64_i$ must therefore be amenable to vacuum-tight connections. The inner surface of the capsule $64_i$ is lined with an electrical insulator, while the external surface of the capsule $64_i$ is electrically conductive.

The target element $60_i$ is preferably spaced apart from and opposite the electron emissive surface of the cathode $50_i$. In one embodiment, the target element $60_i$ is a small beryllium (Be) substrate, coated on the side exposed to the incident electron beam with a thin film or layer of a high-Z material, such as tungsten (W), uranium (U) or gold (Au). As the atomic number of the x-ray emissive material increases, the peak output in the spectral distribution curve of the emitted x-rays, and the characteristic spectral lines of the x-rays, shift to higher energies. The efficiency of x-ray generation is highly dependent on the acceleration voltage provided by the high voltage power supply 80, although independent of the electron beam current. By way of example, when the electrons are accelerated to 30 keV-, a 2.2 micron thick tungsten layer absorbs substantially all of the incident electrons, while transmitting approximately 95% of any 30 keV-, 88% of any 20 keV-, and 83% of any 10 keV x-rays generated in that layer. In this embodiment, the beryllium substrate $60_i$ is 0.5 mm thick. With this configuration, 95% of the x-rays generated in directions normal to and toward the target element $60_i$, and having passed through the tungsten layer, are then transmitted through the beryllium substrate. The x-rays are then directed outward through the x-ray transmissive window of the housing onto a desired region-to-be-treated.

The controller 140 allows each individual x-ray source $20_i$ to be individually controllable. The intensity control circuitry 142 allows user-controlled adjustment of the intensity of the x-ray radiation, and the duration control circuitry 144 allows user-controlled adjustment of the duration of the x-ray radiation. The intensity of the x-rays emitted from a particular x-ray source $20_1$ may be controlled by adjusting either 1) the magnitude of the accelerating voltage provided between the cathode $50_i$ and the target $60_i$ in the x-ray source $20_1$; or 2) the intensity of the electron beam current formed by the electrons emitted from the cathode $50_i$ in the x-ray source $20_i$.

The intensity of the x-rays emitted from an x-ray source $20_i$ is directly proportional to the intensity of the electron beam current in the x-ray source $20_i$, because x-rays are produced when incident electrons from the cathode $50_i$, interacting with the target nuclei, are decelerated and eventually brought to rest. An electron having some initial kinetic energy (provided by the accelerating voltage between the cathode $50_1$ and the target element $60_i$) is decelerated during an encounter with a heavy target nucleus, because of the Coulomb interaction between the electron and the nucleus. The energy lost by the electron appears as x-ray photons, in the form of bremsstrahlung ("braking") radiation. The energies of these x-ray photons correspond to the energy lost by the colliding electron. Increasing the electron beam current therefore results in a directly proportionate increase in x-ray emission. An electron in the incident beam typically loses different amounts of energy in many such encounters with the target nucleus, before the electron is finally brought to rest. The x-rays produced by numerous electrons making a large number of different encounters therefore produce many discrete photons having continuously varying wavelengths, i.e. a continuous bremsstrahlung spectrum is produced.

Figure 2A:
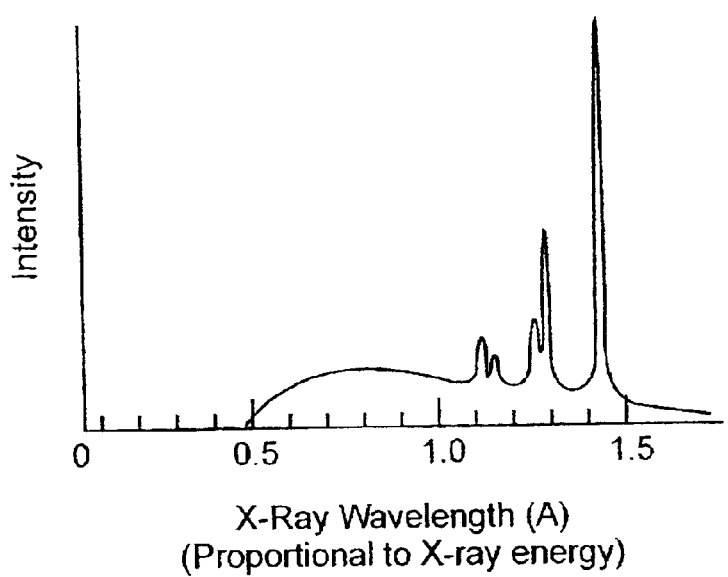
FIG. 2(a) illustrates an x-ray spectrum for a tungsten target that includes a continuous bremsstrahlung spectrum as well as the characteristic spectral lines for tungsten.
Figure 2B:
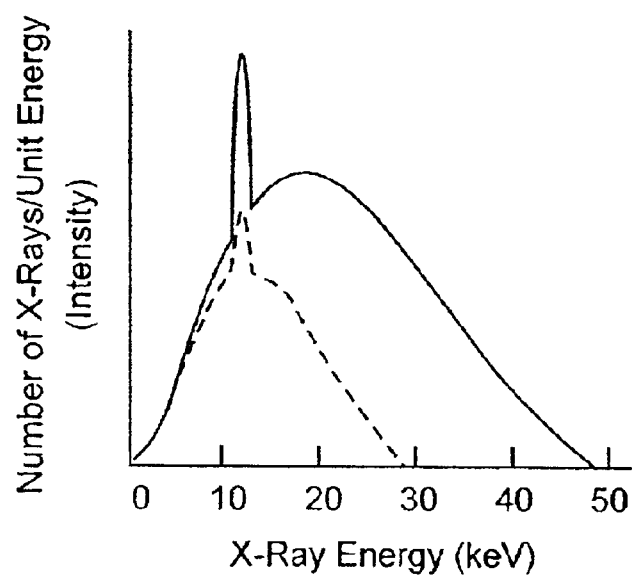
FIG. 2(b) illustrates the continuous bremsstrahlung x-ray spectrum emitted from a tungsten target for two different values of incident electron energy.

FIG. 2(*a*) illustrates an x-ray spectrum for a tungsten target that includes the continuous bremsstrahlung spectrum. FIG. 2(*a*) also includes the characteristic spectral lines for tungsten, in addition to the bremsstrahlung spectrum. These discrete spectral lines are characteristic of the transitions between bound electron energy levels of tungsten, as allowed by the selection rules. When an incident electron passes near an electron in an inner subshell of a target atom, the electron sometimes imparts enough energy to the inner subshell electron so as to remove it from its very negative energy level and eject it from the target atom. The highly excited target atom emits a set of high frequency photons, which produce the characteristic x-ray line spectrum of the atom forming the target material, in this case tungsten.

FIG. 2(*b*) illustrates the continuous bremsstrahlung x-ray spectrum emitted from a tungsten target for four different values of incident electron energy. While increasing the electron beam current results in a directly proportional increase in x-ray emission at all spectral ranges, a change in the acceleration voltage between the cathode $50_1$ and the target $60_i$ results in a total x-ray output variation proportional to the square of the voltage, since the kinetic energies of the electrons are proportional to the square of the accelerating voltage. A corresponding shift in the peak x-ray photon energy is also observed, as illustrated in FIG. 2(*b*).

In the present invention, the intensity control circuitry 142 permits a user to vary the intensity of the x rays emitted by each x-ray source $20_i$ as desired, by adjusting the accelerating voltage provided to each source $20_i$, and/or the electron beam current generated in each source $20_i$. The duration control circuitry 144 permits a user to regulate the time intervals during which the accelerating voltage and the laser radiation is provided to each x-ray source $20_i$.

Figure 3:
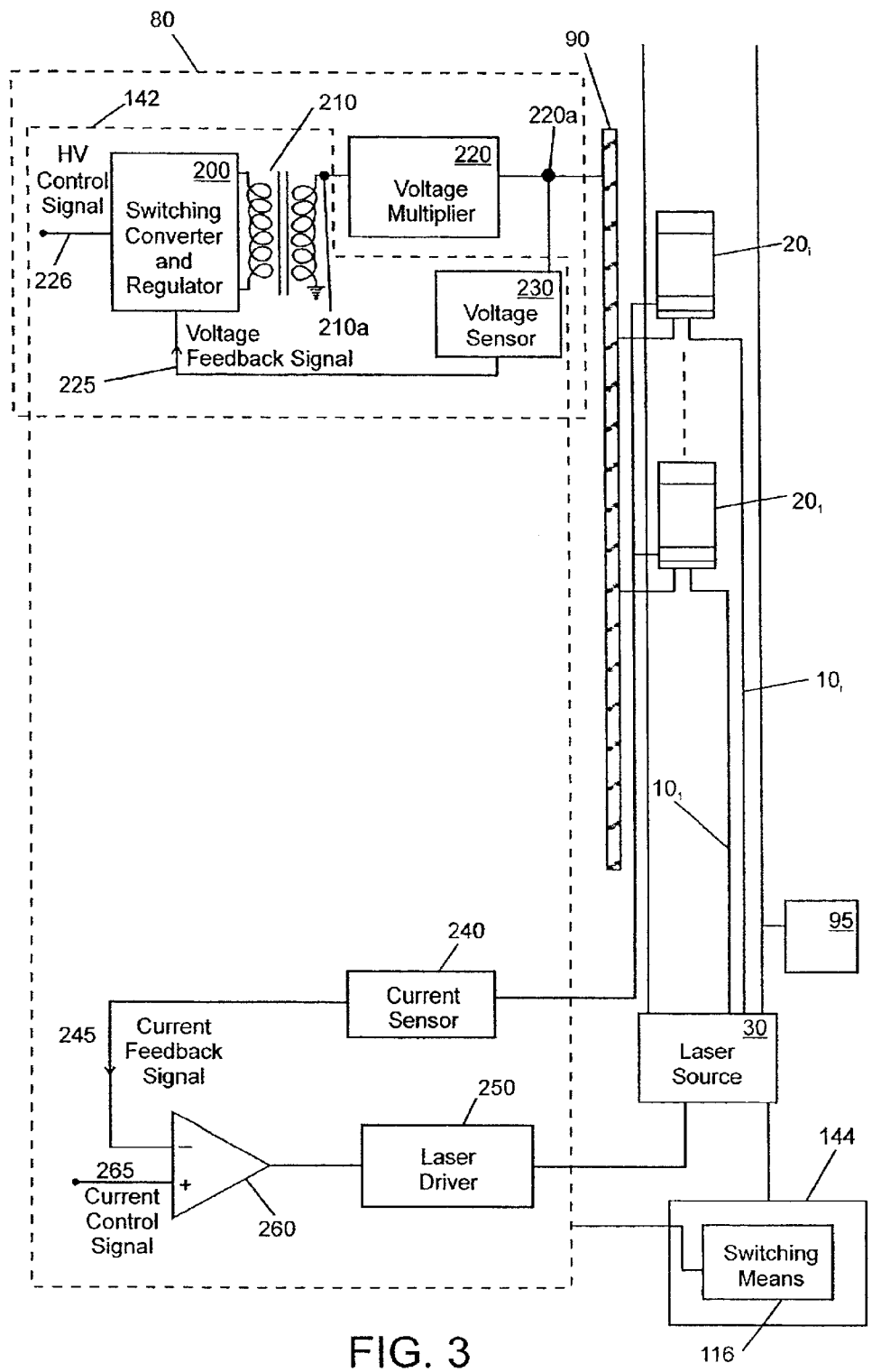
FIG. 3 illustrates one exemplary embodiment of the intensity control circuitry, in accord with the present invention.

FIG. 3 illustrates in more detail one possible embodiment of the intensity control circuitry 142 for controlling the magnitude of the accelerating voltage, in accord with the present invention. As illustrated in FIG. 3, the intensity control circuitry 142 includes a switching converter and regulator 200, and a high voltage transformer 210. The power supply 80 includes a high voltage multiplier 220. The transformer 210 is coupled to a control voltage terminal 220a, which also serves as a high voltage multiplier input terminal. The voltage multiplier 220 and establishes an output voltage at a high voltage terminal 220a. In one embodiment, the voltage multiplier 220 may include a set of series connected diodes and sets of series coupled capacitors (not shown).

A voltage sensor 230 senses the voltage level at the high voltage terminal 220a, and a voltage feedback signal representing the sensed voltage level is sent on line 225 to the regulator 200. The switching converter and regulator 200 establishes a high voltage amplitude feedback loop, in response to a detected difference between the voltage feedback signal on line 225, and an applied high voltage control signal on line 226. The high voltage control signal may be selectively controlled to establish a desired variation of the amplitude of the potential at the high voltage terminal 220a. The output voltage at the high voltage terminal 220a may be controlled by varying the density of the constant energy pulses from the power transformer 210. The output voltage can be electrically compared to the control signal from line 226, and, if the output voltage is too low, the frequency of the energy pulses can be increased. The high voltage terminal 220a is connected to the high voltage conducting cable 90, which provides the regulated output voltage to each cathode $50_i$.

The intensity of the electron beam current generated by a laser-heated thermionic cathode or a photocathode depends, inter alia, on the intensity of the laser beam that impinges upon the cathode $50_i$. The intensity control circuitry 142 may thus include a current sensor 240 coupled to each x-ray source $20_i$, and a laser driver 250 for the laser source 30. The current sensor 240 measures the electron beam current in each x-ray source $20_i$. The laser driver 250 regulates the intensity of the laser beam generated by the laser source 30, so as to vary the intensity of the electron beam current generated by the cathode $50_1$.

The intensity control circuitry 142 may include a difference amplifier 260 which establishes a current feedback loop by driving the laser driver in response to a detected difference between a current feedback signal from the current sensor 240 on line 245, and an applied emission control signal from the difference amplifier on line 265. The emission control signal may be selectively controlled to establish a desired variation in the x-ray tube cathode current.

In one embodiment of the invention, the laser source 30 may be a pulsed laser source, capable of generating sequential pulses of laser light. In this embodiment, the intensity control circuitry 142 may include means for increasing or decreasing the frequency of the pulses of laser light.

The duration control circuitry 144 controls the duration of the emission of the x-rays. The duration control circuitry 144 may include switching means 146 coupled to the high voltage power supply 80. The switching means 146 may selectively turn on and off the voltage provided by the power supply to any desired one of the plurality of x-ray sources, thereby controlling the time interval during which the accelerating voltage is provided to each x-ray source $20_i$. The duration control circuitry 144 may also include means (not shown) for selectively activating the laser source 30, i.e. means for selectively turning on or off the laser source 30, thereby effectively turning on and off one or more of the plurality of laser-driven x-ray sources $20_i$. In one embodiment of the invention, the duration control circuitry 144 may include an optical switching network (not shown) operable to selectively activate and de-activate each of the plurality of x-ray sources $20_i$ by selectively connecting and disconnecting each x-ray source $20_i$ from the laser source 30.

In one embodiment of the invention, the controller 140 includes a mechanical introducer assembly 95 that is operable to selectively insert and withdraw each x-ray source $20_1$ to and from the treatment region. Preferably, the introducer 95 controllably effects reversible displacements of the array of therapeutic radiation sources along the passageway, so as to insert the array into a treatment region, and withdraw the array from the treatment region. For example, the introducer 95 may insert a linear array of sources into a blood vessel in a patient's vascular system. The introducer 95 may include a guide member for guiding and navigating the array of x-ray sources through the blood vessel or other body passageway, and onto a desired treatment region.

Alternatively, the introducer 95 may allow each individual therapeutic radiation source to be independently inserted into, and withdrawn from, the treatment region. In this embodiment, the introducer 95 may allow selective and independent movement of the individual sources relative to each other, along the axes that define the one- or multi-dimensional array of radiation sources. Alternatively, the introducer 95 may allow a planar array of sources to be guided onto a desired treatment region, by mechanically manipulating one linear row or column of sources at a time, in a multi-row or multi-column array of radiation sources.

Because the x-ray sources $20_i$ are individually controllable, a radiation dose distribution can be built up so as to match any desired pattern. For example, each of the plurality of x-ray sources $20_i$ may be selectively switched on for different lengths of time, in a manner deemed appropriate by the surgeon or other radiotherapy professional, and as dictated by the conditions of the patient. Alternatively, the intensity of each x-ray source $20_i$ may be adjusted, so that for example the acceleration voltage and beam current are increased for an x-ray source $20_i$ that is being used to destroy a tumor that is relatively large in size, while the acceleration voltage and beam current are decreased for an x-ray source $20_i$ that is being used to destroy a tumor that is relatively small in size. In some cases, for reasons such as the topology of the treatment regions, it may not be possible for the introducer 95 to position the x-ray sources $20_i$ at an exact, desired location. In these cases, the intensity of an x-ray source $20_i$ may be adjusted according to need. For example, if an x-ray source $20_i$ is located further from a tumor than would be desired, due to a deficiency in the implant process, the accelerating voltage, the electron beam current, and the duration of x-ray emission, can all be increased, in order to build a higher dosage for the treatment region.

In operation, an array of therapeutic radiation sources, preferably x-ray sources, are positioned near a desired treatment region within a patient, using a mechanical introducer. For example, the array may be inserted into a body passageway (such as a blood vessel), and guided through the passageway, until each x-ray source is positioned at a desired location with respect to the treatment region. Each of the plurality of x-ray sources are selectively activated, so as to irradiate the treatment region. Using the controller featured in the present invention, the intensity and duration of the therapeutic radiation generated by each source in an array of sources can be controlled by the user, so as to achieve a desired, predetermined irradiation profile.

Figure 4:
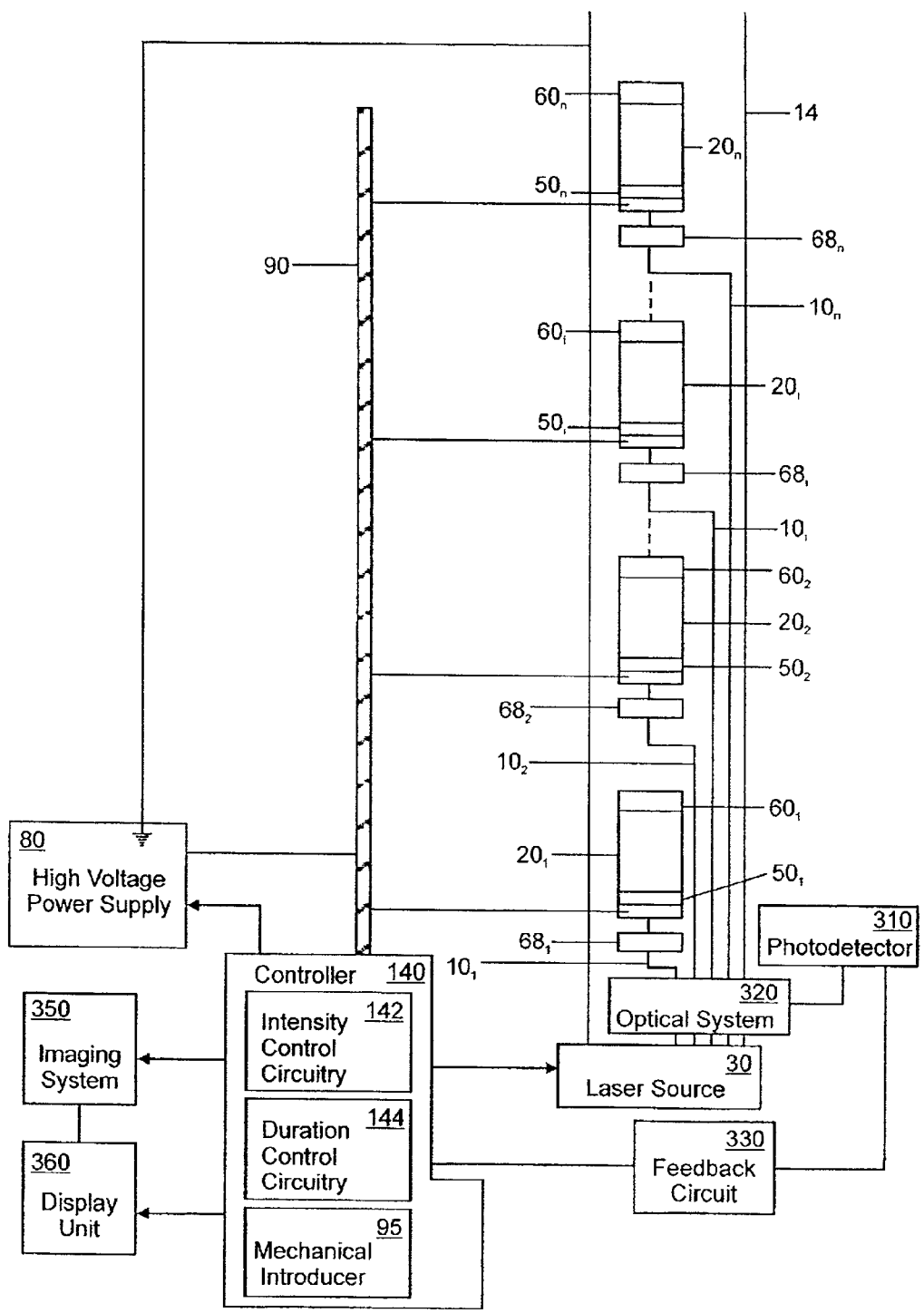
FIG. 4 is a schematic illustration of one embodiment of a controller for an array of therapeutic radiation sources in accordance with the present invention, in which the controller regulates an in situ radiation detecting system and an image-guided surgery system for the array of therapeutic radiation sources.

FIG. 4 is a schematic illustration of another embodiment of a controller 140 for an array of x-ray sources $20_1$ in accordance with the present invention, in which the controller 140 also regulates an in situ radiation detecting system for real time monitoring of the radiation dose distribution. In this embodiment, the controller 140 also regulates an image-guided surgical system that uses images of the treatment region to guide the position of each of the plurality of x-ray sources $20_1$, and permits the surgeon to visualize during the surgical procedure the cumulative dose of radiation delivered by each source $20_i$. A method and apparatus for image-guided radiotherapy is disclosed in U.S. patent application Ser. No. 09/656,878, and is hereby incorporated by reference. The image-guided surgical system includes an imaging system 350 which generates a visual image representing the cumulative dose of radiation delivered by each source $20_i$ to a desired point within the treatment region. The visual image is displayed on the display unit 360, to guide the surgeon during his delivery of therapeutic radiation.

The in situ radiation detection system includes a scintillator $68_i$ disposed along a path of the x-rays emitted by each x-ray source $20_i$. The scintillator $68_1$ is adapted to generate flashes of scintillator light, in response to the x-rays that are incident thereon. The intensity of the scintillator light is proportional to the quantity of the incident x-ray photons, as well as to their energies. In the illustrated embodiment, the scintillator $68_i$ is affixed to the terminating end of the associated fiber optic cable $10_i$. The scintillator $68_i$ is thus arranged so that the x-rays incident on the scintillator $68_i$ are predominantly those x-rays that are emitted from the target element $60_1$ in a backward direction, with respect to the path of the incident electron beam. It should be noted, however, that any configuration that places the scintillator $68_i$ along any path of the emitted x-rays is within the scope of this invention.

A photodetector 210 is placed in optical communication with each scintillator $68_i$. The photodetector 210 converts scintillator light into a signal proportional to the intensity of the scintillator light, and hence indicative of the amount of x-rays emitted by the associated target element $60_i$ and incident on the scintillator $68_1$. The photodetector 210 may be a photomultiplier 210, by way of example. In one form, the photomultiplier may include a plurality of anodes. The radiation detection system may also include an optical system 220 for selectively directing light so that only light from the scintillator $68_i$ is incident on the photodetector 210, and all other types of optical radiation, such as ambient visible light and light from the laser source 30, are filtered out. In one embodiment, the optical system 220 may include a dichroic beam splitter (not shown) and a filter (not shown) disposed between the laser source 30 and each fiber optic cable $10_i$. The photodetector 210 is preferably coupled to a feedback circuit 230, which feeds the indicative signal from the photodetector 210 back to the controller 140. The controller 140 is responsive to the feedback signals from the photodetector 210, to calculate in real time a cumulative dose of the x-rays detected by the scintillator $68_i$. The calculated cumulative dose information may be displayed on a display unit 360, such as a monitor screen. This permits the surgeon or other radiotherapy professional to monitor, in real time, the cumulative dose of the delivered x-rays.

In one form of the invention in which a single optical fiber (having an originating end and a plurality of terminating ends, as mentioned earlier) is used, the controller 140 may include means (not shown) for gating on and off the incident optical radiation from the laser source 30. The intensity of the scintillator light may be measured during the off-times.

In sum, by stringing together a plurality of individually controllable therapeutic radiation sources, and by controlling parameters such as the turn-on time and position of each individual therapeutic radiation source, as well as the duration and intensity of the therapeutic radiation emitted by each source, any desired dose and spatial distribution of the output radiation can be attained. An arbitrarily complex radiation density distribution may be attained over a desired treatment region.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for delivering therapeutic radiation to a treatment region, the system comprising:
    A. an array of therapeutic radiation sources, comprising:
        a. a plurality of therapeutic radiation sources selectively and moveably disposed along an axis so as to form an array,
        wherein each therapeutic radiation source comprises:
            i. an electron source for emitting electrons to generate an electron beam along a beam path; and
            ii. a target element positioned in said beam path, said target element including at least one radiation emissive material adapted to emit therapeutic radiation in response to incident electrons from said electron beam; and
        b. means for providing an accelerating electric field which acts to accelerate electrons generated by said electron source toward said associated target element; and
    B. a controller for selectively operating each therapeutic radiation source so as to generate therapeutic radiation at selected time intervals, said controller comprising:
        a. intensity control circuitry for controlling the intensity of the therapeutic radiation generated by each radiation source; and
        b. duration control circuitry for controlling the duration of the therapeutic radiation generated by each radiation source.

2. A system according to claim 1, wherein said intensity control circuitry comprises programmable means for user-controlled adjustment of at least one of the amplitude of said accelerating voltage and the magnitude of the current formed by said electron beam, for each therapeutic radiation source.

3. A system according to claim 1, wherein said means for providing an accelerating voltage comprises a high voltage power supply having a high voltage terminal, and drive means for establishing an output voltage at said high voltage terminal.

4. A system according to claim 3, wherein said intensity control circuitry comprises:
    a. a control voltage terminal; and
    b. a voltage feedback means for sensing the voltage level at said high voltage terminal and for controlling said voltage level in response to a control voltage signal applied at said control voltage terminal.

5. A system according to claim 1, wherein said duration control circuitry comprises means for selectively activating said means for providing an accelerating voltage.

6. A system according to claim 1, wherein said electron beam is characterized by a current in the approximate range of 1 nA to 1 mA.

7. A system according to claim 1, further comprising a mechanical assembly operable to selectively insert and withdraw each therapeutic radiation source to and from said treatment region.

8. A system according to claim 1, wherein said therapeutic radiation comprises x-rays, and wherein said radiation emissive element comprises an x-ray emissive element.

9. A system according to claim 1, wherein electrons incident on each target element from each electron source are accelerated by said accelerating electric field to energies in the approximate range of 10 kV to 90 kV.

10. A system according to claim 1, wherein said array formed of said plurality of therapeutic radiation sources is adapted for insertion into a vessel for intravascular therapy, and wherein electrons incident on each target element from each electron source are accelerated by said accelerating electric field to energies in the approximate range of about 30 kV to about 40 kV.

11. A system according to claim 1,
wherein at least one electron source comprises a thermionic cathode, said thermionic cathode having an electron emissive surface and being adapted to emit electrons when heated to a sufficient temperature by a laser beam.

12. A system according to claim 1, wherein at least one of said plurality of therapeutic radiation sources comprises a substantially rigid housing enclosing said electron source and said target element and defining a substantially evacuated interior region extending along said electron beam path, said housing comprising a radiation transmissive window wherein therapeutic radiation emitted from said target element is directed through said radiation transmissive window.

13. A system for delivering therapeutic radiation to a treatment region, the system comprising:
A. an array of therapeutic radiation sources, comprising:
   a. a plurality of fiber optical cables, each fiber optical cable having an originating end and a terminating end, each fiber optical cable being adapted for transmitting light incident on said originating end to said terminating end;
   b. a corresponding plurality of therapeutic radiation sources selectively and moveably disposed in an array, each therapeutic radiation source being coupled to the terminating end of a corresponding fiber optical cable;
wherein each therapeutic radiation source comprises:
   i. an electron source, responsive to light transmitted to said terminating end of said corresponding fiber optical cable, for generating electrons, and
   ii. a target element associated with said electron source, said target element including at least one radiation emissive element for emitting therapeutic radiation in response to incident accelerated electrons from said electron source;
c. one or more optical sources, including means for generating for each of said plurality of therapeutic radiation sources a beam of light directed to the originating end of the corresponding fiber optical cable; and
d. means for providing an accelerating voltage between each electron source and each associated target element so as to establish an accelerating electric field which acts to accelerate electrons generated by said electron source toward said associated target element; and
B. a controller for selectively operating each therapeutic radiation source so as to selectively generate therapeutic radiation at selected time intervals, said controller comprising:
   a. intensity control circuitry for controlling the intensity of the therapeutic radiation generated by each radiation source; and
   b. duration control circuitry for controlling the duration of the therapeutic radiation generated by each radiation source.

14. A system according to claim 13, further comprising an in situ radiation detecting system for monitoring in real time the amount of the therapeutic radiation emitted by each therapeutic radiation source, said radiation detecting system comprising:
   a. at least one scintillator disposed along a path of the therapeutic radiation emitted by each therapeutic radiation source and adapted to generate scintillator light in response to the therapeutic radiation incident thereon, wherein the intensity of said scintillator light is proportional to the intensity of said incident therapeutic radiation;
   b. a photodetector in optical communication with said scintillator for converting said scintillator light into a signal indicative of the presence and amount of said incident therapeutic radiation;
   c. a feedback circuit for feeding back said indicative signal to said controller; and
   d. means, responsive to said indicative signal, for calculating in real time a cumulative dosage of said therapeutic radiation.

15. A system according to claim 14, further comprising a display mechanism for real time visual monitoring of said cumulative dosage of said therapeutic radiation.

16. A system according to claim 14, wherein said photodetector comprises a photomultiplier tube.

17. A system according to claim 16, wherein said photomultiplier tube comprises a plurality of anodes.

18. A system according to claim 14, wherein said radiation detection system further comprises an optical system for selectively directing light so that only said scintillator light is incident upon said photodetector, said optical system being adapted for separating said scintillator light from ambient visible light and from optical radiation generated by said one or more light sources.

19. A system according to claim 18, wherein said optical system comprises at least one of dichroic beam splitter and a filter.

20. A system according to claim 14, wherein said one or more optical sources comprises a laser source, and wherein said beam of transmitted light is substantially monochromatic and coherent.

21. A system according to claim 20, wherein said laser source is adapted for generating sequential pulses of laser light.

22. A system according to claim 13, further comprising a switching network operable to selectively activate and de-activate each of said plurality of therapeutic radiation sources.

23. A system according to claim 13, wherein at least one electron source comprises a photocathode having a photoemissive surface, said photocathode being positioned adjacent to the terminating end of the corresponding fiber optical cable and being responsive to portions of said light beam incident thereon from said terminating end to emit electrons from said photoemissive surface.

24. A system according to claim 13, wherein at least one of said plurality of fiber optical cables is enclosed within an electrically conductive, flexible, outer sheath.

25. A system according to claim 13, wherein said duration control circuitry comprises means for selectively activating said one or more optical sources.

26. A system for delivering therapeutic radiation to a treatment region, the system comprising:

A. an array of therapeutic radiation sources, comprising:
  a. at least one fiber optical cable having an originating end and a plurality of terminating ends, said at least one fiber optical cable being adapted for transmitting light incident on said originating end to each of said plurality of terminating ends;
  b. a plurality of therapeutic radiation sources selectively and moveably disposed along an array, each therapeutic radiation source being coupled to a corresponding one of said plurality of terminating ends; wherein each therapeutic radiation source comprises:
    i. an electron source, responsive to light transmitted to said corresponding terminating end of said at least one fiber optical cable, for generating electrons, and
    ii. a target element associated with said electron source, said target element including at least one radiation emissive element for emitting therapeutic radiation in response to incident accelerated electrons from said electron source;
  c. one or more optical sources for generating optical radiation, including means for directing said optical radiation to the originating end of said at least one fiber optical cable; and
  d. means for providing an accelerating voltage between each electron source and each associated target element so as to establish an accelerating electric field which acts to accelerate electrons generated by the electron source toward the associated target element; and
B. a controller for selectively operating each therapeutic radiation source so as to selectively generate therapeutic radiation at selected time intervals, said controller comprising:
  a. intensity control circuitry for controlling the intensity of the therapeutic radiation generated by each radiation source; and
  b. duration control circuitry for controlling the duration of the therapeutic radiation generated by each radiation source.

27. A system according to claim 26, wherein said at least one fiber optical cable comprises not more that one fiber optical cable.

28. A system according to claim 27, further comprising means for gating on and off said optical radiation from said one or more optical sources.

29. A system according to claim 28, further comprising means for measuring the intensity of said scintillator light during the off-times of said gating of said optical radiation from said one or more optical sources.

30. A method for treating a region within a body passageway, including:
  a. inserting an array of x-ray sources into a body passageway;
  b. guiding said array of x-ray sources through said body passageway so as to position each x-ray source at a desired location with respect to said region; and
  c. selectively activating one or more of said x-ray sources, and
  d. controlling the intensity and duration of the x-ray radiation generated by each x-ray source so as to irradiate said region according to a predetermined irradiation profile.

31. A method according to claim 30, wherein said body passageway comprises a blood vessel.

32. A method for treating an anatomical region, comprising:
  a. positioning an array of x-ray sources in proximity to said anatomical region; and
  b. selectively activating one or more of said x-ray sources, and
  c. controlling the intensity and duration of the x-ray radiation generated by each x-ray source so as to irradiate said anatomical region with x-rays; in accordance with a predetermined irradiation profile.

* * * * *

UNITED STATES PATENT AND TRADEMARK OFFICE
CERTIFICATE OF CORRECTION

PATENT NO.    : 6,728,335 B1
DATED         : April 27, 2004
INVENTOR(S)   : Thomson et al.

It is certified that error appears in the above-identified patent and that said Letters Patent is hereby corrected as shown below:

Column 16,
Line 34, after "x-rays", delete ";".

Signed and Sealed this

Seventh Day of December, 2004

JON W. DUDAS
*Director of the United States Patent and Trademark Office*